US007767839B2

(12) United States Patent
Berry et al.

(10) Patent No.: US 7,767,839 B2
(45) Date of Patent: Aug. 3, 2010

(54) PROCESS OF MAKING ALKYL ESTERS OF FREE FATTY ACIDS

(75) Inventors: William Wesley Berry, Lakeland, FL (US); Brian J. Ratigan, Philadelphia, PA (US)

(73) Assignee: Philadelphia Fry-o-Diesel, Inc., Philadelphia, PA (US)

( * ) Notice: Subject to any disclaimer, the term of this patent is extended or adjusted under 35 U.S.C. 154(b) by 141 days.

(21) Appl. No.: 11/467,162

(22) Filed: Aug. 24, 2006

(65) Prior Publication Data

US 2008/0051593 A1 Feb. 28, 2008

(51) Int. Cl.
*C11B 13/00* (2006.01)
(52) U.S. Cl. .................................... 554/174
(58) Field of Classification Search ............... 554/174
See application file for complete search history.

(56) References Cited

U.S. PATENT DOCUMENTS

2005/0158074 A1* 7/2005 Murakami et al. .......... 399/121

OTHER PUBLICATIONS

Chem. Abstr. of IN-2005MU00423, Jun. 2005.*
Christie, William W., *Preparation of Ester Derivatives of Fatty Acids for Chromatographic Analysis*, Advances in Lipid Methodology—Two, pp. 69-111 (1993). Accessed online Aug. 8, 2007 @ http://www.lipidlibrary.co.uk/topics/ester_93/file.pdf.

* cited by examiner

*Primary Examiner*—Deborah D Carr
(74) *Attorney, Agent, or Firm*—Woodcock Washburn, LLP

(57) ABSTRACT

A process of preparing alkyl esters of free fatty acids, including, but not limited to, biodiesels is described herein.

47 Claims, 2 Drawing Sheets

PROCESS OF MAKING ALKYL ESTERS OF FREE FATTY ACIDS

TECHNICAL FIELD

The present invention relates generally to processes for preparing alkyl esters of free fatty acids (FFAs), particularly processes directed to preparing biodiesel.

BACKGROUND

Biodiesel generally is a fuel, often employed as a petroleum diesel replacement fuel made from fats, oils, and greases. Biodiesel is technically defined as a fuel that comprises mono-alkyl esters of FFAs derived from vegetable oils or animal fats and which meets the requirements of ASTM D 6751, the entire disclosure of which is incorporated herein by reference.

Conventional biodiesel production generally uses, as a feedback, oils and/or fats that are primarily composed of triglycerides (TGs) and may further contain small amounts of FFAs.

Fats and oils are generally insoluble in water but soluble in many organic solvents. They generally have lower densities than water, and may have consistencies at ambient temperature (about 25° C.) of solid, semi-solid, or clear liquid. When they are solid, appearing at room temperature, they are referred to as "fats," and when they are liquid at that temperature, they are called "oils." For simplification, the term "oil" is generally used herein to refer to both fats and oils that originate from animal or vegetable sources (as opposed to petroleum-based oils).

Oils are classified as "lipids" which is a category that embraces a broad group of chemical substances. In addition to TGs, the term "lipids" also includes monoglycerides (MGs), diglycerides (DGs), FFAs and other substances, including, but not limited to, fatty alcohols and tocopherols. Other than the FFAs, crude vegetable oils generally contain up to about two percent total of these minor components. Animal fats generally contain smaller amounts of these other substances than do vegetable oils.

Structurally, the TGs which make up fats and oils generally consist of three fatty acids attached to one glycerol molecule. If all three fatty acids are identical, the TG is generally referred to as a "simple" TG. The more common forms, however, are "mixed" TGs in which two, three, or more different fatty acids are present in the fatty acid. The general chemical structure of TGs is shown in Scheme 1 below, wherein structure IA illustrates a simple TG and structure IB illustrates a mixed TG. The R groups on the TGs are typically linear hydrocarbon chains comprising up to about 21 carbons and optionally up to about 6 double bonds.

SCHEME 1

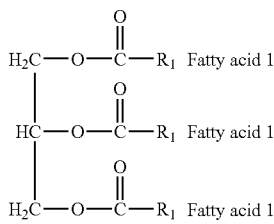

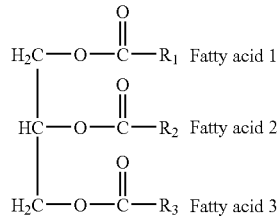

Oils may also include partial degradation products derived from TGs, such as MGs, exemplified by general formula IIA and IIB in Scheme 2 below, and DGs, exemplified by general formulae IIC and IID in Scheme 2.

SCHEME 2

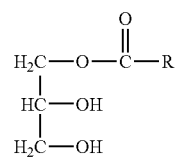

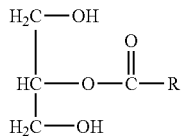

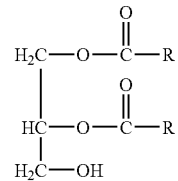

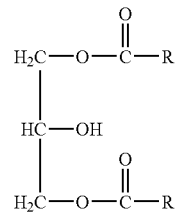

Conversion of oils to alkyl esters of FFAs (including, but not limited to, biodiesel) is typically accomplished by a process of transesterification, wherein the glycerol portion of a glyceride, e.g., a TG, is replaced with an alcohol, generally methanol or ethanol. The reaction is generally base catalyzed and carried out at atmosphere pressure. Conventional biodiesel production processes generally do not work well for esterification/transesterification of feedback containing levels of FFAs that are higher than about 2% because FFAs and bases generally react under such conditions to form soaps. For feedback containing more than about 2% FFA, a two-step procedure is generally required, typically including an acid-catalyzed pretreatment targeting conversion of FFA to esters, followed by a base-catalyzed reaction to convert remaining glycerides to esters, both steps generally performed at atmospheric pressure.

Animal fats from rendering operations, as well as used cooking oils, including, for example, restaurant trap grease, provide a potentially attractive feedstock for biodiesel production. The expression "restaurant trap grease" generally refers to grease that has traveled down a drain at a restaurant often captured in a grease interceptor, or "trap," before it enters a sanitary sewer, as well as grease generally produced by cooking or food preparation establishments. However, such feedstock typically contains high levels of FFAs as a result of hydrolytic degradation of TGs, generally resulting from microbial, chemical or thermal reaction. Hydrolysis of a TG molecule is depicted in Scheme 3 below.

SCHEME 3

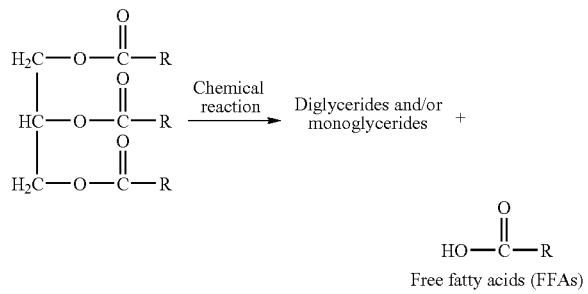

Elevated levels of FFAs generally complicate, increase process time, and raise the cost of conversion to biodiesel.

Restaurant trap grease is a low cost waste material. It is, however, a complex and challenging feedstock from the standpoint of impurities, variability and processing requirements. It varies widely in composition, often including, in varying proportions, fats, oils, and greases as well as food particles, dirt, water and other materials that are carried down drains.

There is a need for a process capable of converting feedstocks, such as restaurant trap grease, which contain higher levels of FFAs and which may provide a cost-effective way to convert feedstock containing used oils, such as restaurant trap grease, into esters of FFAs, including, but not limited to, biodiesel.

SUMMARY

According to some embodiments of the invention, a process for preparing biodiesel comprises contacting a feedstock with an alcohol and an acid catalyst to form a mixture; reacting the mixture at a temperature from about 80° C. to about 200° C. and at greater than atmospheric pressure to form a reacted mixture; and separating from the reacted mixture a composition comprising an alkyl ester of a FFA.

According to some embodiments of the invention, a process for preparing an alkyl ester of a FFA comprises contacting a feedstock with an alcohol and an acid catalyst to form a mixture; reacting the mixture at a temperature from about 80° C. to about 200° C. and at greater than atmospheric pressure to form a reacted mixture; and separating from the reacted mixture a composition comprising an alkyl ester of a FFA.

According to some embodiments, there is provided a biodiesel fuel produced according to the above process.

The details of some embodiments of the invention are set forth in the description below. Other features, objects, and advantages of the invention will be apparent from the description and from the claims.

BRIEF SUMMARY OF THE DRAWINGS

FIG. 1 depicts a time course and product distribution for an esterification of restaurant trap grease at 115° C. and 90 psi.

DETAILED DESCRIPTION

Figure 1:
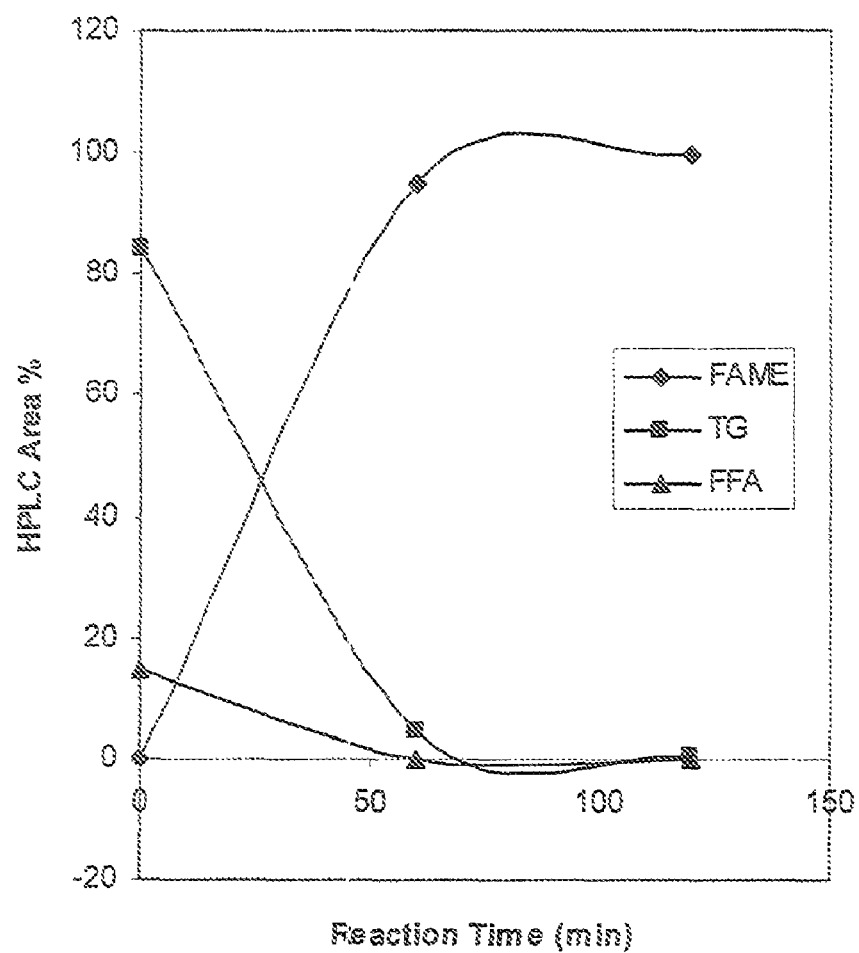
FIG. 1 depicts a time course and product distribution for an esterification of restaurant trap grease at 115° C. and 80 psi.

According to some embodiments, exemplified below in Scheme 4, a feedstock is converted to a composition comprising an alkyl ester of a FFA by reaction of the feedstock with an alcohol and an acid catalyst at a temperature from about 80° C. to about 200° C. According to some embodiments, a process of converting a feedstock to biodiesel comprises reaction of the feedstock with an alcohol and an acid catalyst. The feedstock employed in the process of the invention may comprise any composition comprising glycerides and FFAs in any proportion. The process may accomplish esterification of FFAs as well as transesterification of glycerides.

SCHEME 4

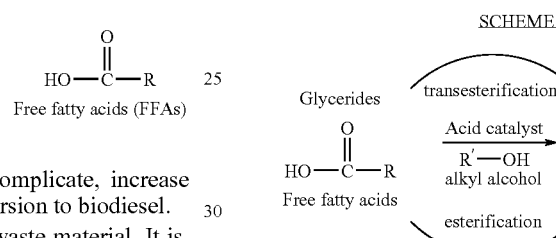

According to some embodiments, the feedstock comprises a used oil. Used oils include, but are not limited to, restaurant trap grease, recovered used cooling oils, such as fryer oils, or animal fats, including, but not limited to, tallow, poultry, lard, or the like from conventional rendering facilities. The feedstock may be composed entirely of used oils, or may contain such used oils as one component in a mixture that contains other components such as, for example, first-use oils and virgin oils. Alternatively, the feedstock may comprise no used oils. The percentage of FFAs in restaurant trap grease varies widely. Non-limiting examples of percentage variations of FFA in restaurant trap grease include, but are not limited to, from about 10 percent to as much as 100 percent, from about 15% to about 95%, or from about 20% to about 90%.

In addition to waste grease that is termed "restaurant trap grease," by virtue of originating from a restaurant and being collected in a trap, there are other sources of waste materials that are similar in character to restaurant trap grease and that may be used as feedstock. Non-limiting examples include grease from food processing companies, company cafeterias, or the like, and grease other than that collected in a trap, for example, greases like float grease; float grease is generally grease that has gone through a sewer system and is subsequently separated at a wastewater treatment plant.

According to some embodiments, the feedstock contains FFAs in an amount up to 100% by weight of the feedstock. According to some embodiments, the feedstock contains greater than 5 or greater than 15% by weight of the feedstock. According to other embodiments, the feedstock contains greater than 25% or greater than 50% by weight of the feedstock. According to some embodiments, the feedstock contains greater than 75%, or 85% or 95% by weight of the feedstock. According to some embodiments, the processing may be carried out via reaction in a reactor. The step of contacting the feedstock with an alcohol and an acid catalyst may be carried out by bringing the components in contact in any order or combination. As non-limiting examples, an alcohol and an acid catalyst may be added, separately or together, to the feedstock, or the feedstock may be mixed with an alcohol and then contacted with an acid catalyst, or the feedstock may be mixed with an acid catalyst and then contacted with an alcohol.

Further, a portion of one component of the feedstock may be reacted in a suitable reactor with the other component. The feedstock, alcohol, and the catalyst may be added separately to a reactor, or may be mixed prior to adding to the reactor. Suitable reactors may include a mechanism to adjust and a mechanism to regulate the temperature of the process; the adjusting and regulating mechanisms may be the same mechanism. Suitable reactors also may include a mechanism to agitate or stir the reaction mixture. Suitable reactors may also be capable of being sealed so that the reaction may be carried out under greater than atmospheric pressure. Typical reactors for carrying out the process include, but are not limited to, stirred tank reactors, plug flow reactors, pump type reactors wherein the fluids are mixed in a high energy section, column-type reactors which have internals that provide for continuous or intermittent mixing, and other reactor systems know in the art. The process may be carried out in either a batch or continuous mode.

The step or separating a composition comprising an alkyl ester of a FFA from the reacted mixture may be carried out by separating part, all, or substantially all of the water and glycerin that are formed as byproducts of the process, and removing part, all, or substantially all of the alcohol employed in the process. Separating the glycerin and water from the reacted mixture may be carried out by allowing a fraction comprising water and glycerin to phase separate in the reacted mixture and then separating the phase containing the water and glycerin. Decanting the reacted mixture, cannulating or removing the fraction containing water and glycerin from the reacted mixture via a tap or outlet in the reactor in which the process is carried out, transferring the reacted mixture to a separation vessel, including, but not limited to, a gravity settler or centrifuge separatory funnel, allowing phase separation and removing the phase containing water and glycerin are non-limiting examples of methods to separate the glycerin and water from the reacted mixture. Separation may also be carried out with other liquid/liquid separation systems including, but not limited to, centrifuges, hydroclones and the like.

Removing the alcohol employed in the process from the reacted mixture may be carried out by distillation or similar process. Distillation to remove the alcohol may also serve to remove part of the water formed as a byproduct of the esterification reaction. Distillation to remove the alcohol may be carried out at or greater than atmospheric pressure or by reducing the pressure in the reactor to atmospheric pressure while the temperature of the reacted mixture is above its boiling point at atmospheric pressure, or a pressure greater or less than atmospheric pressure.

The process may optionally further comprise isolating biodiesel from the composition comprising an alkyl ester of a FFA. Isolating biodiesel may be carried out by distilling the composition at atmospheric pressure or at reduced pressure including, but not limited to, reducing the pressure so that it is above or below atmospheric pressure.

Distillation may comprise methods such as "flash" distillation or "fractional" distillation. "Flash" distillation is generally a single stage process similar to evaporation wherein the composition is heated, under vacuum, and the ester portion of the composition is vaporized, and then subsequently condensed to recover the distilled ester. Fractional distillation serves to separate the desired product from higher and lower boiling components of the composition comprising an alkyl ester of a FFA, which is separated from the reacted mixture. Fractional distillation typically employs a distillation column that may contain trays, packing or other mechanisms for increasing the theoretical plates in the column and thereby facilitates separation of the desired biodiesel product from higher and lower boiling components.

According to some embodiments, when the alcohol employed in the process is methanol, a biodiesel product may be isolated by distillation at atmospheric pressure and collection of biodiesel product that distills in a boiling point range from about 320° C. to about 360° C. According to some embodiments, a biodiesel product may be isolated by distillation at a pressure in the range from about 1 torr to about 10 torr. In some embodiments, when the alcohol employed in the process in methanol, a biodiesel product may be isolated by distillation at a pressure of about 2 torr and collection of product that distillation at a boiling point range from about 188° C. to about 340° C. (atmospheric equivalent temperature (AET)).

According to some embodiments, residual acid, if present in the composition comprising an alkyl ester of a FFA, may be neutralized prior to distillation. The neutralization of residual acid may be carried out, by reaction with a base. Non-limiting examples of bases are alkoxide bases, including, but not limited to, sodium methoxide, sodium hydroxide, potassium hydroxide, calcium oxide, or other alkaline or alkali materials that are useful neutralizing agents, and combinations of the foregoing.

The alcohol used in the process may be a $C_1$-$C_4$ alcohol. Non-limiting examples of $C_1$-$C_4$ alcohols are methanol, ethanol, propanol, isopropanol, n-butanol, sec-butanol, isobutanol or tert-butanol, or any mixture thereof. The alcohol may be a single alcohol or a mixture of two or more alcohols. In some embodiments, the alcohol is methanol or ethanol or a mixture thereof. As non-limiting examples, the alcohol may be used in an amount from about 12% to about 100%, or from about 20% to about 100%, or from about 20% to about 50% by weight of the feedstock. The alcohol may also be used in amounts based on the volume of the feedstock, from about 12% to about 100%, or from about 20% to about 100%, or from about 20% to about 50% by volume of the feedstock. Reaction times and catalyst concentrations may be adjusted for varying proportions of the alcohol.

The acid catalyst used in the process may be sulfuric acid, an alkyl or aryl sulfonic acid, a cation exchange resin, a fluorinated ionomer resin, similar products, and combinations thereof. Cation exchange resins include, but are not limited to, AMBERLYST® resins (for example, AMBERLYST® 15; Chemical Abstracts No. [39389-20-3]), which are generally polymer based ion exchange resins that typically comprise functionalized styrene divinylbenzene copolymers with different surface properties and porostiites, and generally supplied as gellular or macroreticular spherical beads. Such polymer based ion exchange resins generally have acidic functional groups that are generally of the sulfuric acid type. Fluorinated ionomer resins include, but are not limited to, NAFION® (Chemical Abstracts No. [31175-20-9]). In some embodiments, the acid catalyst may be sulfuric acid.

The acid catalyst may be dissolved or suspended in the alcohol prior to mixing with the feedback or the acid catalyst may be added separately. The acid catalyst may be a single acid catalyst material or may be a mixture of two or more different acid catalysts. The catalyst is used in an amount sufficient to afford a desired reaction time under the temperature and pressure conditions employed for the reaction.

According to some embodiments, when the acid catalyst is sulfuric acid, it may be employed in an amount from about 1 gram to about 50 grams per liter of the feedstock used in the reaction, or from about 5 grams to about 50 grams per liter of the feedstock used in the reaction, or from about 5 grams to about 40 grams per liter of the feedstock used in the reaction, or from about 10 grams to about 40 grams per liter of the feedstock used in the reaction. An acid catalyst other than sulfuric acid may be used in the reaction in an amount per liter of the feedstock used that yields about the same amount of hydrogen ions as the above ranges of sulfuric acid; as a non-limiting example, an amount of catalyst that would yield from about 10 mmol to about 500 mmol, or from about 50 mmol to about 500 mmol, or from about 50 mmol to about 400 mmol, or from about 100 mmol to about 400 mmol of hydrogen ions for reaction catalysis per liter of feedstock may be used.

According to some embodiments, when the acid catalyst is sulfuric acid, it may be employed in an amount from about 1 gram to about 50 grams per liter of the alcohol used in the reaction, or from about 5 grams to about 50 grams per liter of the alcohol used in the reaction, or from about 5 grams to about 40 grams per liter of the alcohol used in the reaction, or from about 10 grams to about 40 grams per liter of the alcohol used in the reaction. An acid catalyst other than sulfuric acid may be used in the reaction in an amount per liter of the alcohol used that yields about the same amount of hydrogen ions as the above ranges of sulfuric acid; as a non-limiting example, an amount of catalyst that would yield from about 10 mmol to about 500 mmol, or from about 50 mmol to about 500 mmol, or from about 50 mmol to about 400 mmol, or from about 100 mmol to about 400 mmol, of hydrogen ions for reaction catalysis per liter of alcohol may be used.

According to some embodiments, the acid catalyst is sulfuric acid in an amount that is about 6.25 grams per liter of alcohol used in the reaction. According to some embodiments, the acid catalyst is sulfuric acid in an amount that is about 6.25 grams per liter of alcohol used in the reaction and is dissolved in the alcohol prior to mixing with the feedstock or with a partially reacted feedstock.

Proportions of the catalyst and the alcohol employed in the process may be optimized based on factors that include, but are not limited to, the reactor design, reactor size, throughput desired, proportion of FFAs in the feedstock, feedstock characteristics, and operating cost.

The temperature at which the process described herein is carried out may be from about 80° C. to about 200° C., or from about 80° C. to about 150° C., or from about 100° C. to about 200° C., or from about 100° C. to about 150° C., or from about 115° C. to about 150° C., or from about 115° C. to about 125° C. According to some embodiments, the process is carried out at a temperature of about 115° C. The temperature may be held constant during the process or may be varied during the process, including, but not limited to, varying the temperature according to a gradient.

The pressure at which the process is carried out may be a pressure sufficient to prevent the reaction mixture from boiling. Non-limiting examples of such pressure include, but is not limited to, a pressure equal to, or greater than, the vapor pressure of the reaction mixture at the temperature at which the process is carried out. Additionally, the pressure at which the process is carried out may be from about 50 psi to about 200 psi, or from about 80 psi to about 200 psi, or from about 100 psi to about 200 psi, or from about 80 psi to about 150 psi, or from about 100 psi to about 150 psi, or from about 80 psi to about 100 psi. The pressure at which the process is carried out may be held constant during the process or may be varied, such as, without limitation, according to a gradient. According to some embodiments, the pressure during the reaction may be approximately equal to the vapor pressure of the reaction mixture or approximately equal to vapor pressure of the alcohol in the reaction mixture. According to some embodiments, the pressure during the process may be greater than the vapor pressure of the reaction mixture or greater than vapor pressure of the alcohol in the reaction mixture. According to some embodiments, the pressure at which the process is carried out may be about 85 psi.

The process may be carried out in less than twenty-four hours, or in less than twelve hours, or in less than eight hours, or in less than four hours, or in less than two hours, or in less than one hour, in less than 0.5 hour or in less than 0.25 hour. In some embodiments, the process is carried out in from about one minute to about eight hours, or from about 0.10 hour to about eight hours, or from about 0.25 hour to about eight hours, or from about one hour to about eight hours, or from about two hours to about six hours, or from about two hours to about four hours.

According to some embodiments, the process may be carried out in two or more stages. A first stage comprises contacting a feedstock with an alcohol and an acid catalyst to form a mixture: and reacting the mixture at a temperature from about 80° C. to about 200° C. to form a reacted mixture. In some embodiments, the second stage of the process comprises contacting the partially reacted feedstock with a second alcohol and a second acid catalyst to form a second mixture; and reacting the second mixture at a temperature from about 80° C. to about 200° C. to form a reacted second mixture. A composition comprising an alkyl ester of a FFA is then separated from the reacted second mixture. The process optionally further comprises isolating biodiesel from the composition comprising the alkyl ester of a FFA.

According to some embodiments, the first stage mixture is reacted for a time interval from about one minute to about four hours, or from about 0.10 hour to about four hours, or from about 0.25 hour to about four hours, or from about 0.5 hour to about four hours, or from about one hour to about three hours, or from about one hour to about two hours. Between the completion or near-completion of the first stage of the process and the start of the second stage of the process, the water and glycerin formed during the first stage are separated or substantially separated from the reacted mixture to provide a composition comprising a partially reacted feedstock. The expression "partially reacted feedstock" as used herein means that a portion of the free carboxyl groups in the feedstock are esterified and also a portion of the ester groups in the feedstock are transesterified to replace the alkoxy group present in the unreacted feedstock with an alkoxy group contributed by the alcohol that is used in the process, e.g., a methyl ester when the alcohol used is methanol.

Separating the glycerin and water may be carried out by allowing a fraction containing water and glycerin to phase separate in the reacted mixture and then removing the fraction. Decanting the reacted mixture, cannulating or removing the glycerin and water via a tap or outlet in the reactor in which the process is carried out are non-limiting examples of methods of separating the glycerin and water. In some embodiments, removing or substantially removing means at least about 30% of water and glycerin is removed from the reacted mixture. Also, as stated earlier, the water formed during the esterification reaction may be partially removed by co-distillation when the alcohol is removed by distillation, as well as being removed by separation of a fraction containing water and glycerin.

According to some embodiments, the second stage mixture is reacted for a time interval from about one minute to about four hours, or from about 0.10 hour to about four hours, or from about 0.25 hour to about four hours, or from about 0.5 hour to about four hours, or from about one hour to about three hours, or from about one hour to about two hours. Separation of a composition comprising an alkyl ester of a FFA from the second reacted mixture may be carried out by separating part or all of the water and glycerin that are formed a byproduct of the second stage of the process and optionally removing part or all of the alcohol employed in the process. Separating the glycerin and water may be carried out by allowing a fraction containing water and glycerin to phase separate settle to the bottom of the reacted mixture and removing the fraction. Decanting, cannulating or removing the glycerin and water via a tap or outlet in the reactor in which the process is carried out are non-limiting examples of methods of separating the glycerin and water. Removing alcohol employed in the process may be carried out by distillation or similar process. Distillation to remove the alcohol may be carried out at atmospheric pressure or at reduced pressure. Part of the water formed during the esterification reaction may co-distill when the alcohol is removed by distillation.

According to some embodiments, the process may further comprise a third stage, wherein the composition comprising a simply alkyl ester of a FFA that is separated from the reacted second mixture is contacted with a third alcohol and a third acid catalyst to form a third mixture. The third mixture is subsequently reacted at a temperature from about 80° C. to about 200° C. to form a reacted third mixture. A composition comprising an alkyl ester of a FFA is then separated from the reacted third mixture. Additional stages that follow the process of the third stage may be implemented until a desired yield of the alkyl ester of the FFA is obtained.

The alcohol and the amount of the alcohol used in different stages of the process may be the same or different. According to some embodiments, the same alcohol is used in some or all process stages.

Also, the catalyst and the amount of the catalyst used in different stages of the process may be the same or different. According to some embodiments, the same acid catalyst is used in both or all process stages. This means that either the same compound is used for the acid catalyst or after the acid catalyst is used in one stage it is recycled and used again in another stage, or both. According to some embodiments, the same amount of acid catalyst is used in both or all process stages.

The temperature during different stages of the process may be the same or different. Also, the pressure during different stages of the process may be the same or different. According to some embodiments, the temperature is the same in some or all process stages. According to some embodiments, the pressure is the same or all process stages. According to some embodiments, both the temperature and the pressure are the same in some or all process stages.

The invention will be described in greater detail by way of specific examples. The following examples are offered for illustrative purposes and are not intended to limit the invention in any manner. Those of skill in the art will readily recognize a variety of noncritical parameters which can be changed or modified to yield essentially or substantially the same results. It will be understood that numerical values appearing in the Examples are subject to limits in precision of measurement and are thus to some extent approximate.

Example 1

Restaurant trap grease (2 L) was added to a reactor with an agitator and a steam heat source. Methanol/$H_2SO_4$ (prepared by adding $H_2SO_4$ (6.25 g) to methanol (1 L)) was added to the reactor to form a mixture with the trap grease. The reactor was sealed to maintain pressure during heating. The mixture was heated with agitation to 115° C., and maintained at that temperature for 60 minutes. The reactor pressure was 80 psi. After 60 minutes the pressure in the reactor was released and some of the methanol and some of the water formed during the reaction was allowed to boil off of the mixture (total 741 mL/592 g). The heat to the reactor was turned off and the reactor was allowed to cool to below approximately 65° C. Remaining water and any glycerin formed during the reaction were then decanted from the partially reacted mixture. Methanol/$H_2SO_4$ (prepared by adding $H_2SO_4$ (6.25 g) to methanol (1 L)) was added to the reactor. The reactor was sealed and the mixture was heated with agitation to 115° C., and maintained at 115° C. and 80 psi for 60 minutes. After 60 minutes, the pressure in the reactor was released and some of the methanol and some to the water formed in the reaction was allowed to boil off of the mixture. Additional water and glycerin formed during the second stage of reaction was decanted from the reaction product. Vacuum (25 in. Hg) was then applied to the reactor and substantially all of the excess methanol used in the reaction and dissolved water in the ester solution were removed under reduced pressure. A total of 835 mL (665 g) of methanol and water was removed by boiling off and distillation. The reactor was allowed to cool overnight. The crude product was removed from the reactor and placed in a separator funnel and allowed to settle (about 60 minutes). The bottom fraction (121 mL/150 g) was separated and removed. The upper layer (2184 mL/1921.9 g) was collected and the acid number was checked. Sodium methylate (4.5 mL/4.95 g) was added to neutralize any unreacted FFAs. The neutralized bottom fraction distilled at reduced pressure (1.5 torr) and the top approximate 90% of the distillation was collected in a temperature range of 135-160° C. Both the first and second part of the reaction was monitored by high performance liquid chromatography (HPLC) analysis of samples removed from the reaction mixture at time points of 0, 60 minutes and 120 minutes (time points are identified for the total 120 minute time for the two 60 minute portions of the reaction). The HPLC methods was carried out according to the method of Haas et al., The Enzymatic Hydrolysis of Triglyceride-Phospholipid Mixtures in an Organic Solvent. JAOCS 72:519-525 (1995), with the exception that a Sedex75 detector (Sedere, Inc. Cedex, France) was employed (detector temperature was 40° C. and the gain control was set to 2). The HPLC analyses are shown in terms of percent of product (fatty acid methyl ester (FAME)) and starting materials FFAs and triglycerides (TG)) in Table 1 and in FIG. 1. The distilled product (1962 mL/1726.6 g) was analyzed under ASTM D-6751 and the results are provided below in Table 2.

TABLE 1

| Time Point (min) | FAME (Area %) | TG (Area %) | FFA (Area %) |
| --- | --- | --- | --- |
| 0 | 0 | 84.4 | 15 |
| 60 | 94.9 | 4.8 | 0.1 |
| 120 | 99.4 | 0.6 | 0 |
| Distilled | 100 | 0 | 0 |

TABLE 2

| Method | Results (approximate) |
|---|---|
| D 6584 - Free and Total Glycerin in B-100 | 0.006 mass % Free Glycerin |
| | 0.201 mass % Monoglyceride |
| | 0.000 mass % Diglyceride |
| | 0.000 mass % Triglyceride |
| | 0.058 mass % Tot. Glycerin |
| D 93 - Flash-Point by Pensky-Martens Closed Cup Tester | 171° C. |
| D 2709 - Water and Sediment | <0.05 vol. % |
| D 445 - Kinematic Viscosity | 4.470 cSt @ 40° C. |
| D 874 - Sulfated Ash | 0.003 mass % |
| D 5453 - Total Sulfur by Ultraviolet Fluorescence | 3 ppm (wt/wt) |
| D 130 - Copper Corrosion | 1a |
| D 5773 - Cloud Point | 2° C. |
| D 524 - Carbon Residue, Ramsbottom | <0.010% Carbon Residue |
| D 664 - Acid Number of Petroleum Products by Potentiometric Titration | 0.18 mg KOH/gram |
| D 4951 - Phosphorous by ICP | <0.0005 mass % |
| D 1160 - Distillation at Reduced Press. Reported in Atmospheric Equivalent Temperatures (AET) | 10 mm Hg |
| | 266° C. IBP AET |
| | 346° C. 5% Rec. AET |
| | 348° C. 10% Rec. AET |
| | 348° C. 20% Rec. AET |
| | 349° C. 30% Rec. AET |
| | 349° C. 40% Rec. AET |
| | 350° C. 50% Rec. AET |
| | 350° C. 60% Rec. AET |
| | 351° C. 70% Rec. AET |
| | 351° C. 80% Rec. AET |
| | 352° C. 90% Rec. AET |
| | 354° C. 95% Rec. AET |
| | 356° C. FBP AET |
| | 99.0 Vol. % |
| | 10 mm Hg |

Example 2

Restaurant trap grease (453.5 g) and vegetable oil (439.1 g) were added to a reactor equipped with an agitator and a steam heat source was added. Methanol/$H_2SO_4$ (395.7 g) was added to the reactor to form a mixture with the trap grease and vegetable oil. The methanol/$H_2SO_4$ had been prepared earlier by adding $H_2SO_4$ (6.25 mL) to methanol (1 L). The reactor was sealed to maintain pressure during heating. The mixture was heated with agitation to 115° C., and maintained at that temperature for 60 minutes. The reactor pressure was 90 psi. After 60 minutes the pressure in the reactor was released and some of the methanol and some of the water formed during the reaction was allowed to boil off of the mixture (total 271.3 g). The heat to the reactor as turned off and the reactor was allowed to cool to below approximately 65° C. The contents of the reactor were transferred to a separatory funnel and allowed to settle (about 60 minutes). A bottom layer separated and was removed (24.4 g). The upper layer (740.6 g) was transferred to a second reactor. Methanol/$H_2SO_4$ (333.3 g) (prepared by adding $H_2SO_4$ (6.25 g) to methanol (1 L)) was added to the reactor. The reactor was sealed and the mixture was heated with agitation to 115° C., and maintained at 115° C. and 90 psi for 60 minutes. After 60 minutes, the pressure in the reactor was released and some of the methanol and some to the water formed in the reaction was allowed to boil off of the mixture. Vacuum (25 in. Hg) was then applied to the reactor and substantially all of the methanol and the water formed in the reaction were removed under reduced pressure. A total of 284.7 g of methanol and water was removed by the combination of boiling off and distillation. The reactor was allowed to cool overnight. The crude product was removed from the reactor and placed in a separatory funnel and allowed to settle (about 60 minutes). The bottom fraction (9.6 g) was separated and removed. The upper layer (677.3 g) was collected and the acid number was checked. Sodium methylate was added to neutralize any unreacted FFAs. The neutralized bottom fraction distilled a reduced pressure (1.5 torr) and the top 90% of the distillation was collected (667.3 g) in a temperature range of 135-160° C.

Figure 2:
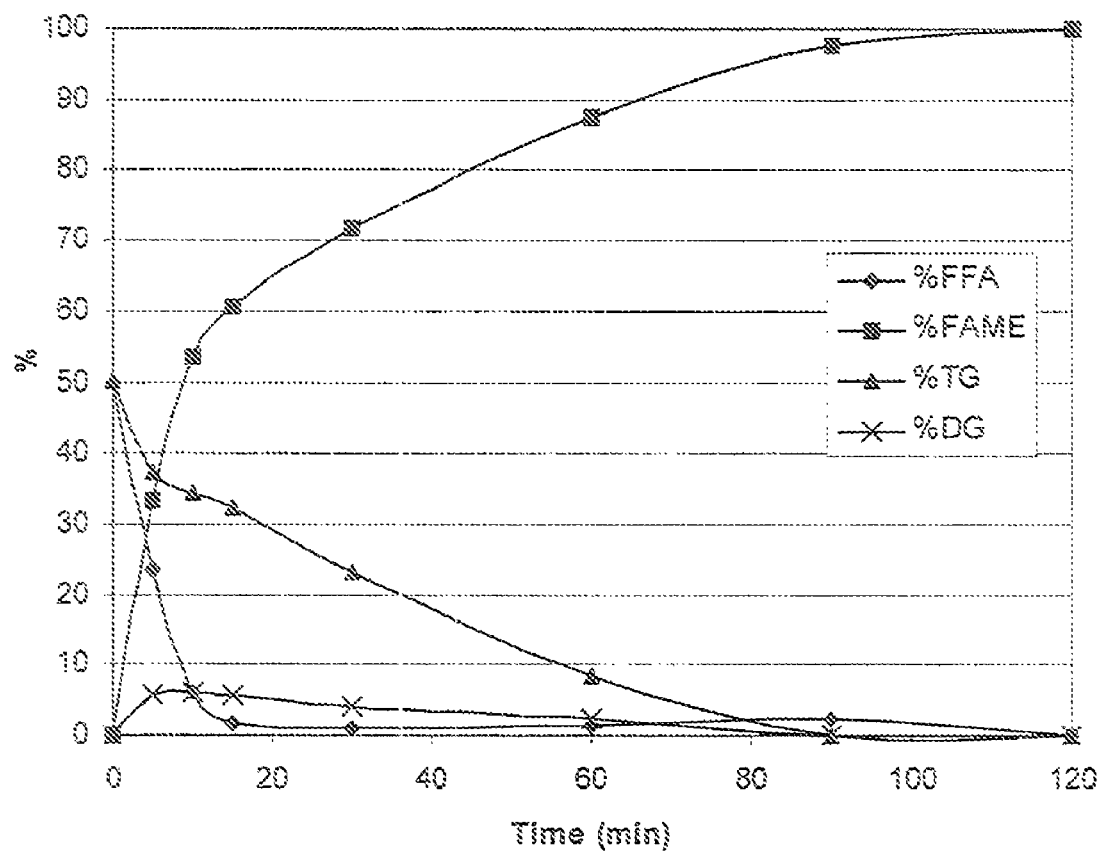

Both the first and second part of the reaction was monitored by HPLC analysis of samples removed from the reaction mixture at time points of 0, 5, 10, 15, 30 and 60 minutes for the first part of the reaction and at 90 and 120 minutes for the second part (time points are identified for the total 120 minute time for the two 60 minute portions of the reaction). The HPLC analysis are shown in terms of percent of product FAME and starting materials FFA, TG and DG (diglycerides), in Table 3 below and in FIG. 2.

TABLE 3

| Time Point | FFA (area %) | FAME (area %) | TG (area %) | DG (area %) |
|---|---|---|---|---|
| First part of reaction | | | | |
| 0 | 49.7 | 0 | 50.3 | 0 |
| 5 | 23.5 | 33.4 | 37.5 | 5.63 |
| 10 | 6.14 | 53.6 | 34.2 | 6.04 |
| 15 | 1.56 | 60.5 | 32.3 | 5.63 |
| 30 | 0.957 | 71.6 | 23.3 | 4.13 |
| 60 | 1.49 | 87.6 | 8.56 | 2.32 |
| Second part of reaction | | | | |
| 90 | 2.32 | 97.7 | 0 | 0 |
| 120 | 0 | 100 | 0 | 0 |

A number of embodiments of the invention have been described. Nevertheless, it will be understood that various modifications, in addition to those described herein, may be made without departing from the spirit and scope of the invention. For example, the acid catalyst, if heterogenous, may comprise a stationary phase and the reaction may be carried out by passing the reaction mixture over or through the stationary catalyst while otherwise maintaining the reaction temperature and pressure conditions. Accordingly, such modifications are also intended to fall within the scope of the appended claims. Each reference cited in the present application, including all patents, publications and books, is incorporated herein by reference in its entirety.

What is claimed is:

1. A process for preparing a biodiesel comprising alkyl esters of free fatty acids, comprising:
    at least partially reacting a trap grease feedstock comprising greater than about 25% by weight free fatty acids, glycerides, or a combination thereof with a $C_1$-$C_4$ alcohol and an acid catalyst at a temperature of between about 80° C. and about 200° C. and at a pressure greater than atmospheric pressure, to form a reacted mixture comprising alkyl esters of the free fatty acids, the glycerides, or a combination thereof; and
    distilling the reacted mixture to produce a composition comprising at least a portion of the alkyl esters of the free fatty acids, the glycerides, or a combination thereof.

2. The process of claim 1 further comprising removing from the reacted mixture at least a portion of unreacted alcohol, water, or a combination thereof.

3. The process of claim 1 further comprising removing from the reacted mixture at least a portion of unreacted free fatty acids, glycerides, or a combination thereof.

4. The process of claim 1 further comprising removing glycerin from the reacted mixture.

5. The process of claim 1, wherein the feedstock comprises greater than about 50% by weight free fatty acid.

6. The process of claim 1, wherein the feedstock comprises greater than about 95% by weight free fatty acid.

7. The process of claim 1, wherein the reaction is performed at a pressure sufficient to prevent the mixture from boiling.

8. The process of claim 1, wherein the reaction is performed at a pressure from about 80 psi to about 200 psi.

9. The process of claim 1, wherein the reaction is performed at a pressure from about 80 psi to about 150 psi.

10. The process of claim 1, wherein the reaction is performed at a pressure from about 80 psi to about 100 psi.

11. The process of claim 1, wherein the reaction is performed at a temperature from about 80° C. to about 150° C.

12. The process of claim 1, wherein the reaction is performed at a temperature from about 115° C. to about 150° C.

13. The process of claim 1, wherein the reaction is performed at a temperature from about 115° C. to about 125° C.

14. The process of claim 1 wherein the reaction is performed at a temperature from about 115° C. to about 125° C. and a pressure from about 80 psi to about 100 psi.

15. The process of claim 1, wherein the feedstock further comprises a first use or virgin oil.

16. The process of claim 1 wherein the feedstock further comprises float grease.

17. The process of claim 1, wherein the feedstock further comprises at least one additional used oil.

18. The process of claim 1, wherein the acid catalyst comprises sulfuric acid, an alkyl or aryl sulfonic acid, a cation exchange resin, a fluorinated ionomer resin, or a combination thereof.

19. The process of claim 1, wherein the distillation is carried out at a pressure of between about 1 and about 10 torr.

20. The process of claim 19, wherein the distillation is carried out at a pressure of about 1.5 torr.

21. The process of claim 1 wherein the distillate is collected at a temperature of between about 135° C. and about 160° C.

22. The process of claim 1 further comprising reacting, as a second reaction, at least a portion of unreacted free fatty acids, glycerides, or a combination thereof from the reaction of the trap grease feedstock with the $C_1$-$C_4$ alcohol and the acid catalyst, with a second $C_1$-$C_4$ alcohol and a second acid catalyst at a temperature of between about 80° C. and about 200° C. and at a pressure greater than atmospheric pressure.

23. The process of claim 22, wherein the second reaction is performed at a pressure sufficient to prevent the reacted mixture from boiling.

24. The process of claim 22, wherein the second reaction is performed at a pressure from about 80 psi to about 200 psi.

25. The process of claim 22, wherein the second reaction is performed at a pressure from about 80 psi to about 150 psi.

26. The process of claim 22, wherein the second reaction is performed at a pressure from about 80 psi to about 100 psi.

27. The process of claim 22, wherein the second reaction is performed at a temperature from about 80° C. to about 150° C.

28. The process of claim 22, wherein the second reaction is performed at a temperature from about 115° C. to about 150° C.

29. The process of claim 22, wherein the second reaction is performed at a temperature from about 115° C. to about 125° C.

30. The process of claim 22, wherein the second reaction is performed at a temperature from about 115° C. to about 125° C. and a pressure from about 80 psi to about 100 psi.

31. The process of claim 22, wherein the second acid catalyst is sulfuric acid, an alkyl or aryl sulfonic acid, a cation exchange resin, a fluorinated ionomer resin, or a combination thereof.

32. The process of claim 22 further comprising reacting, as a third reaction, at least a portion of unreacted free fatty acids, glycerides, or a combination thereof, from the second reaction, with a third $C_1$-$C_4$ alcohol and a third acid catalyst at a temperature of between about 80° C. and about 200° C. and at pressure a of greater than atmospheric pressure.

33. The process of claim 32, wherein the third reaction is performed at a pressure sufficient to prevent the reacted mixture from boiling.

34. The process of claim 32, wherein the third reaction is performed at a pressure from about 80 psi to about 200 psi.

35. The process of claim 32, wherein the third reaction is performed at a pressure from about 80 psi to about 150 psi.

36. The process of claim 32, wherein the reaction is performed at a pressure from about 80 psi to about 100 psi.

37. The process of claim 32, wherein the reaction, the second reaction, third reaction, or a combination thereof are reacted at substantially similar pressures.

38. The process of claim 32, wherein the third reaction is performed at a temperature from about 80° C. to about 150° C.

39. The process of claim 32, wherein the third reaction is performed at a temperature from about 115° C. to about 150° C.

40. The process of claim 32, wherein the third reaction is performed at a temperature from about 115° C. to about 125° C.

41. The process of claim 32, wherein the third reaction is performed at a temperature from about 115° C. to about 125° C. and a pressure from about 80 psi to about 100 psi.

42. The process of claim 32, wherein the reaction, the second reaction, the third reaction, or a combination thereof are performed at substantially similar temperatures.

43. The process of claim 32, wherein the $C_1$-$C_4$ alcohol, the second $C_1$-$C_4$ alcohol, the third $C_1$-$C_4$ alcohol, or a combination thereof are the same.

44. The process of claim 32, wherein the third acid catalyst is sulfuric acid, an alkyl or aryl sulfonic acid, a cation exchange resin, a fluorinated ionomer resin, or a combination thereof.

45. The process of claim 32, wherein the acid catalyst, the second acid catalyst, the third acid catalyst, or a combination thereof are the same.

46. A composition comprising an alkyl ester of a free fatty acid, a glyceride, or a combination thereof formed according to the process of claim 1.

47. A biodiesel composition formed according to the process of claim 1.

* * * * *

UNITED STATES PATENT AND TRADEMARK OFFICE
CERTIFICATE OF CORRECTION

| | | |
|---|---|---|
| PATENT NO. | : 7,767,839 B2 | |
| APPLICATION NO. | : 11/467162 | |
| DATED | : August 3, 2010 | |
| INVENTOR(S) | : William Wesley Berry and Brian J. Ratigan | |

It is certified that error appears in the above-identified patent and that said Letters Patent is hereby corrected as shown below:

Title page, item [73], Assignee: should read as follows: Philadelphia Fry-o-Diesel, Inc.

Signed and Sealed this
Twenty-eighth Day of August, 2012

David J. Kappos
*Director of the United States Patent and Trademark Office*